United States Patent
Li et al.

(10) Patent No.: US 11,493,468 B2
(45) Date of Patent: *Nov. 8, 2022

(54) METHOD FOR PREPARING NITROGEN OXIDE GAS SENSOR BASED ON SULFUR-DOPED GRAPHENE

(71) Applicant: SHANGHAI INSTITUTE OF MICROSYSTEM AND INFORMATION TECHNOLOGY, CHINESE ACADEMY OF SCIENCES, Shanghai (CN)

(72) Inventors: Tie Li, Shanghai (CN); Lianfeng Guo, Shanghai (CN); Chen Liang, Shanghai (CN); Yuelin Wang, Shanghai (CN)

( * ) Notice: Subject to any disclaimer, the term of this patent is extended or adjusted under 35 U.S.C. 154(b) by 39 days.

This patent is subject to a terminal disclaimer.

(21) Appl. No.: 17/116,523

(22) Filed: Dec. 9, 2020

(65) Prior Publication Data

US 2021/0102910 A1    Apr. 8, 2021

Related U.S. Application Data

(62) Division of application No. 15/774,007, filed as application No. PCT/CN2016/070283 on Jan. 6, 2016, now Pat. No. 10,908,107.

(30) Foreign Application Priority Data

Nov. 11, 2015 (CN) .......................... 201510764605.2

(51) Int. Cl.
| | | |
|---|---|---|
| G01N 27/00 | (2006.01) | |
| G01N 27/12 | (2006.01) | |
| C23C 16/22 | (2006.01) | |
| G01N 33/00 | (2006.01) | |

(52) U.S. Cl.
CPC .......... *G01N 27/125* (2013.01); *C23C 16/22* (2013.01); *G01N 33/0037* (2013.01)

(58) Field of Classification Search
USPC ........................................ 324/464, 71.1, 693
See application file for complete search history.

*Primary Examiner* — Vincent Q Nguyen
(74) *Attorney, Agent, or Firm* — Global IP Services; Tianhua Gu

(57) ABSTRACT

The present disclosure provides a method for preparing nitrogen oxide gas sensor based on sulfur-doped graphene. The method includes: 1) providing graphene and a micro heater platform substrate, and transferring the graphene onto the micro heater platform substrate; 2) putting the micro heater platform substrate covered with the graphene into a chemical vapor deposition reaction furnace; 3) performing gas feeding and exhausting treatment to the reaction furnace by using inert gas; 4) simultaneously feeding inert gas and hydrogen gas into the reaction furnace at a first temperature; 5) feeding inert gas, hydrogen gas and sulfur source gas into the reaction furnace at a second temperature for reaction to perform sulfur doping to the graphene (21); and 6) stopping feeding the sulfur source gas, and performing cooling in a hydrogen gas and insert gas shielding atmosphere.

11 Claims, 6 Drawing Sheets

METHOD FOR PREPARING NITROGEN OXIDE GAS SENSOR BASED ON SULFUR-DOPED GRAPHENE

CROSS REFERENCE TO RELATED APPLICATIONS

This application is a divisional application of U.S. Ser. No. 15/774,007 having 371(c) date Aug. 7, 2018; the U.S. Ser. No. 15/774,007 is the US national stage of PCT/CN2016/070283 filed on Jan. 6, 2016, which claims the priority of the CN201510764605.2 filed on Nov. 11, 2015; the above-mentioned applications are incorporated herein by reference.

TECHNICAL FIELD

The present disclosure belongs to the technical field of sensors, and in particular relates to a method for preparing nitrogen oxide gas sensor based on sulfur-doped graphene.

BACKGROUND

Nitrogen dioxide is a type of toxic gas, which not only pollutes the environment, but also jeopardizes human health. Nitrogen dioxide will turn into nitric acid when combining with vapor, which results in nitric acid type acid rain. Acid rain will corrode buildings, destroy crops and degrade forests. Nitrogen dioxide is very harmful to human bodies. Once inhaled by human body, nitrogen dioxide can be diffused into deep capillary tracheas of respiratory tracts and pulmonary alveoli, and is slowly dissolved in water on surfaces of pulmonary alveoli and produces nitrous acid and nitric acid, which will cause fierce irritation and corrosion to pulmonary tissues, cause pulmonary congestion and edema and possibly cause pulmonary fibrosis under serious situations. After entering human bodies, nitrite will combine with hemoglobin and produce methemoglobin, which will result in tissue hypoxia, dyspnea and central nerve injuries; and the harm of nitrogen dioxide to pregnant women and children is more serious. Therefore, accurate and low-cost detection for concentration of nitrogen dioxide gas is especially important.

Graphene is a novel two-dimensional material discovered by Andre Geim and Konstantin Novoselov, physicists of University of Manchester, United Kingdom in 2004. Since the thickness is equal to the thickness of a single-atom layer (0.335 nm), graphene has excellent performance such as high strength and flexibility, transparency and conductivity, and graphene is widely concerned about by people in fields such as of high-performance electronic devices, gas sensors, photoelectric devices, compound materials, field emission materials and energy storage. Especially since graphene has very large specific surface area and great gas adsorption ability, it provides an ideal material for manufacturing high-sensitivity gas sensors. However, as proved by researches on graphene gas sensors, intrinsic graphene which is widely adopted at present as a gas-sensitive material makes a cross response to various different gases, and it is difficult to realize high-selectivity gas sensors.

SUMMARY

The present disclosure provides a method for preparing nitrogen oxide gas sensor based on sulfur-doped graphene, solving the problems that intrinsic graphene widely adopted at present as a gas-sensitive material makes a cross response to various different gases and it is difficult to realize high-sensitivity gas sensors.

The present disclosure provides a method for preparing nitrogen oxide gas sensor based on sulfur-doped graphene, and the method comprises the following steps:

1) providing graphene and a micro heater platform substrate, and transferring the graphene onto the micro heater platform substrate;

2) putting the micro heater platform substrate covered with the graphene into a chemical vapor deposition reaction furnace;

3) performing gas feeding and exhausting treatment to the reaction furnace by using inert gas;

4) simultaneously feeding inert gas and hydrogen gas into the reaction furnace at a first temperature;

5) feeding inert gas, hydrogen gas and sulfur source gas into the reaction furnace at a second temperature for reaction to perform sulfur doping to the graphene; and 6) stopping feeding the sulfur source gas, and performing cooling to the reaction furnace in a hydrogen gas and insert gas shielding atmosphere.

As a preferred solution of the method for preparing nitrogen oxide gas sensor based on sulfur-doped graphene provided by the present disclosure, in step 1), the graphene is intrinsic graphene.

As a preferred solution of the method for preparing nitrogen oxide gas sensor based on sulfur-doped graphene provided by the present disclosure, in step 1), the micro heater platform substrate is a single micro heater platform or a wafer level substrate.

As a preferred solution of the method for preparing nitrogen oxide gas sensor based on sulfur-doped graphene provided by the present disclosure, in step 1), a test electrode and a heater are provided on the micro heater platform substrate and the graphene at least covers the test electrode.

As a preferred solution of the method for preparing nitrogen oxide gas sensor based on sulfur-doped graphene provided by the present disclosure, in step 1), the graphene is transferred onto the micro heater platform substrate by adopting a direct transfer method or PMMA method.

As a preferred solution of the method for preparing nitrogen oxide gas sensor based on sulfur-doped graphene provided by the present disclosure, in step 3), the flow rate of the inert gas is 500 sccm-5000 sccm, and the gas feeding and exhausting treatment time is 2 min-30 min.

As a preferred solution of the method for preparing nitrogen oxide gas sensor based on sulfur-doped graphene provided by the present disclosure, in step 4), the first temperature is 200° C.-700° C.; the flow rate of mixed gas of the hydrogen gas and the inert gas is 100 sccm-5000 sccm; and the mixing ratio of the hydrogen gas to the inert gas is 10%-90%.

As a preferred solution of the method for preparing nitrogen oxide gas sensor based on sulfur-doped graphene provided by the present disclosure, in step 5), the second temperature is 300° C.-900° C.; the flow rate of the inert gas is 500 sccm-5000 sccm, the flow rate of the hydrogen gas is 10 sccm-100 sccm and the flow rate of the sulfur source gas is 0.5 sccm-50 sccm; and the doping time is 10 min-50 min.

As a preferred solution of the method for preparing nitrogen oxide gas sensor based on sulfur-doped graphene provided by the present disclosure, the sulfur source gas comprises one or more of hydrogen sulfide and carbonyl sulfide.

As a preferred solution of the method for preparing nitrogen oxide gas sensor based on sulfur-doped graphene provided by the present disclosure, in step 5), temperature is increased from the first temperature to the second temperature, the temperature is kept at the second temperature for 5 min-20 min and then the sulfur source gas is fed into the reaction furnace.

As a preferred solution of the method for preparing nitrogen oxide gas sensor based on sulfur-doped graphene provided by the present disclosure, in step 6), the flow rate of the inert gas is 50 sccm-300 sccm and the flow rate of the hydrogen gas is 10 sccm-40 sccm.

The method for preparing nitrogen oxide gas sensor based on sulfur-doped graphene provided by the present disclosure has the following beneficial effects: a wafer level substrate may be adopted in the method for preparing the nitrogen oxide gas sensor based on sulfur-doped graphene provided by the present disclosure, which can realize wafer level preparation, the level of batch preparation is achieved, and the production cost is greatly reduced. The nitrogen oxide gas sensor based on sulfur-doped graphene provided by the present disclosure has relatively high sensitivity and selectivity to nitrogen oxide gas molecules, can effectively reduce influences of other gases such as vapor on detection and can improve the detection accuracy.

DESCRIPTION OF COMPONENT MARK NUMBERS

Figure 1:
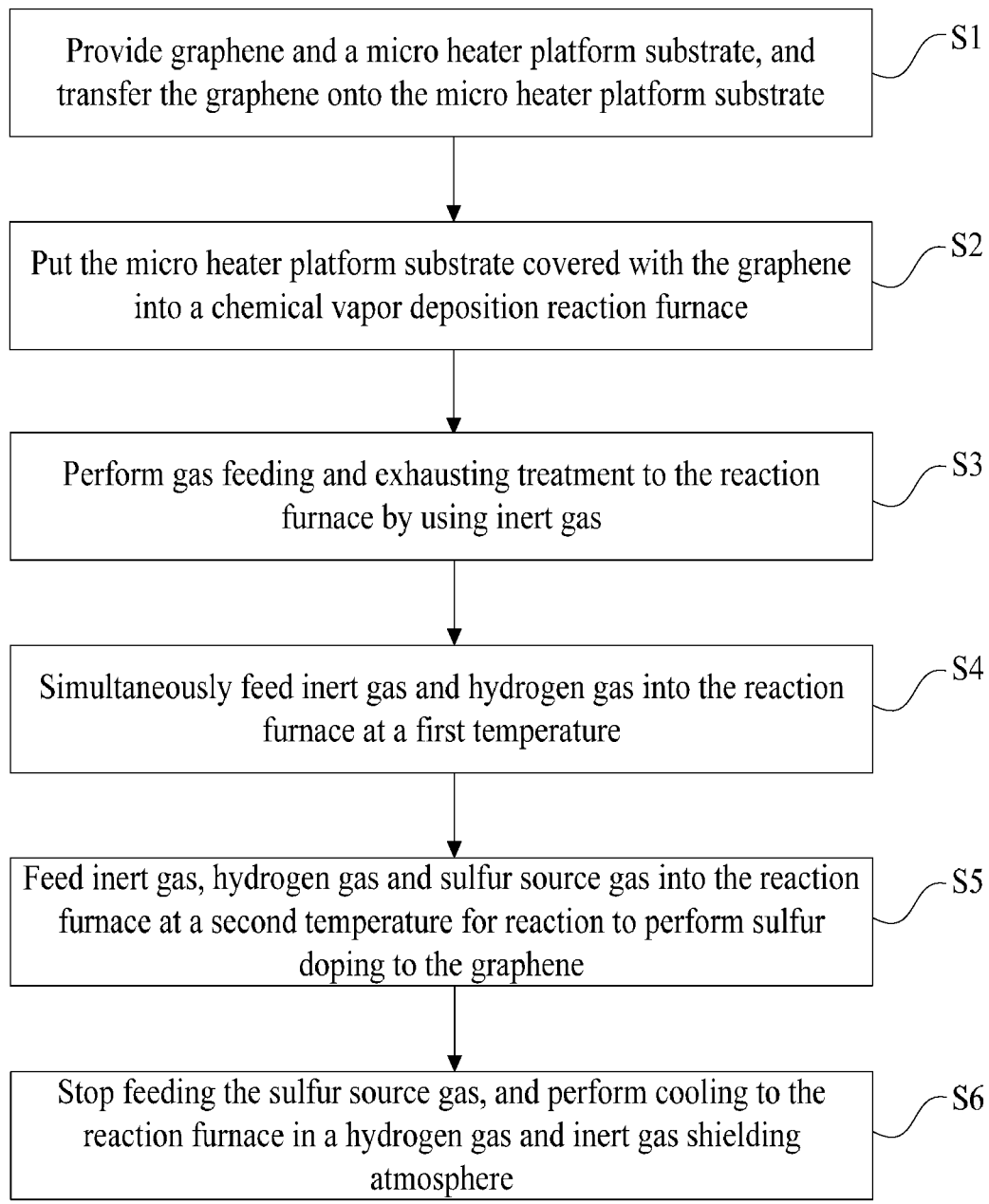
FIG. 1 illustrates a flowchart of a method for preparing nitrogen oxide gas sensor based on sulfur-doped graphene provided by the present disclosure.

20 Copper substrate
21 Intrinsic graphene
22 Corrosion solution
23 Micro heater platform substrate
24 Sulfur-doped graphene
25 Test electrode
26 Heater
27 PMMA
S1-S6 Steps

DETAILED DESCRIPTION OF THE PREFERRED EMBODIMENTS

The implementation modes of the present disclosure will be described below through specific examples. One skilled in the art can easily understand other advantages and effects of the present disclosure according to content disclosed in the description. The present disclosure may also be implemented or applied through other different specific implementation modes. Various modifications or variations may be made to all details in the description based on different points of view and applications without departing from the spirit of the present disclosure.

Please refer to FIG. 1 to FIG. 4. It needs to be stated that the drawings provided in the following embodiments are just used for schematically describing the basic concept of the present disclosure, thus only illustrate components only related to the present disclosure and are not drawn according to the numbers, shapes and sizes of components during actual implementation, the configuration, number and scale of each component during actual implementation therefor may be freely changed, and the component layout configuration therefor may be more complex.

Please refer to FIG. 1, the present disclosure provides a method for preparing a nitrogen oxide gas sensor based on sulfur-doped graphene, and the method comprises the following steps:

1) providing graphene and a micro heater platform substrate, and transferring the graphene onto the micro heater platform substrate;

2) putting the micro heater platform substrate covered with the graphene into a chemical vapor deposition reaction furnace;

3) performing gas feeding and exhausting treatment to the reaction furnace with inert gas;

4) simultaneously feeding inert gas and hydrogen gas into the reaction furnace at a first temperature;

5) feeding inert gas, hydrogen gas and sulfur source gas into the reaction furnace at a second temperature for reaction to perform sulfur doping to the graphene; and 6) stopping feeding the sulfur source gas, and performing cooling to the reaction furnace in a hydrogen gas and inert gas shielding atmosphere.

In step 1), please referring to step S1 in FIG. 1, graphene and a micro heater platform substrate are provided, and the graphene is transferred onto the micro heater platform substrate.

As an example, the graphene is intrinsic graphene. Preferably, the graphene may be but not limited to intrinsic graphene grown on a copper substrate.

As an example, the micro heater platform substrate may be a single micro heater platform and may also be a wafer level substrate; and when the micro heater platform substrate is a wafer level substrate, the wafer level substrate may be but not limited to 4-inch, 8-inch, 12-inch and 16-inch wafers batch-manufactured industrially.

As an example, a test electrode and a heater are provided on the micro heater platform substrate, and the graphene at least covers the test electrode. The test electrode and the heater are not in direct contact, and the test electrode and the heater may be located on different surfaces of the micro heater platform substrate, or located on the same surface of the micro heater platform substrate; when the test electrode and the heater are located on the same surface of the micro heater micro heater platform substrate, the test electrode and the heater are isolated through an insulating layer; and the graphene at least covers the test electrode. In one example, the micro heater platform substrate comprises a first surface and a second surface which are opposite to each other, the test electrode is located on the first surface of the micro heater platform substrate and the heater is located on the second surface of the micro heater platform substrate; and the graphene is transferred to the first surface of the micro heater platform substrate and covers the test electrode and the first surface of the micro heater platform substrate.

As an example, the test electrode may be but not limited to an interdigital electrode.

As an example, the graphene may be transferred onto the micro heater platform substrate by adopting a direct transfer method, or the graphene may also be transferred onto the micro heater platform substrate by adopting a PMMA (polymethyl methacrylate) method.

In step 2), please referring to step S2 in FIG. 1, the micro heater platform substrate covered with the graphene is put into a chemical vapor deposition reaction furnace.

In step 3), please referring to step S3 in FIG. 1, gas feeding and exhausting treatment is performed to the reaction furnace by using inert gas.

As example, the flow rate of the inert gas is 500 sccm-5000 sccm, and the gas feeding and exhausting treatment time is 2 min-30 min.

In step 4), please referring to S4 in FIG. 1, inert gas and hydrogen gas are simultaneously fed into the reaction furnace at the first temperature.

As an example, the first temperature is 200° C.-700° C.; the flow rate of mixed gas of the hydrogen gas and the inert gas is 100 sccm-5000 sccm; and the mixing ratio of the hydrogen gas to the inert gas is 10%-90%. Hydrogen gas is fed into the reaction furnace at the first temperature, a reducing atmosphere may be provided to the internal environment of the reaction furnace, and it is applicable to reduce the micro heater platform substrate and the graphene to prevent them from being oxidized.

In step 5), please referring step S5 in FIG. 1, insert gas, hydrogen gas and sulfur source gas are fed into the reaction furnace at the second temperature for reaction to perform sulfur doping to the graphene.

As an example, the second temperature is 300° C.-900° C.; the flow rate of the inert gas is 500 sccm-5000 sccm, the flow rate of the hydrogen gas is 00 sccm-100 sccm and the flow rate of the sulfur source gas is 0.5 sccm-50 sccm; and the doping time is 10 min-50 min.

As an example, the sulfur source gas may be hydrogen sulfide, carbonyl sulfide, hydrogen sulfide, or carbonyl sulfide.

As an example, temperature is increased from the first temperature to the second temperature, the temperature is kept at the second temperature for 5 min-20 min and then the sulfur source gas is fed into the reaction furnace.

In step 6), please referring to step S6 in FIG. 1, feeding the sulfur source gas is stopped, and cooling is performed to the reaction furnace in a hydrogen gas and inert gas shielding atmosphere As an example, the flow rate of the inert gas is 50 sccm-300 sccm and the flow rate of the hydrogen gas is 00 sccm-40 sccm.

The method for preparing the nitrogen oxide gas sensor based on sulfur-doped graphene provided by the present disclosure will be described below through specific embodiments.

Figure 2A:
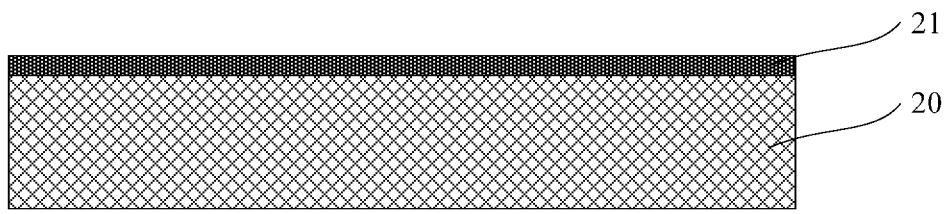
FIG. 2a to FIG. 2g illustrate structural schematic diagrams in each step of a method for preparing a nitrogen oxide gas sensor based on sulfur-doped graphene provided by embodiment 1 of the present disclosure.

Embodiment 1 a) Intrinsic graphene 21 grown on a copper substrate 20 is selected, as illustrated in FIG. 2a.

b) The intrinsic graphene 21 is transferred onto a micro heater platform substrate 23 by using a direct transfer method. In this embodiment, the micro heater platform substrate 23 is a single micro heater platform substrate, as illustrated in FIG. 2b to FIG. 2e.

Figure 2B:
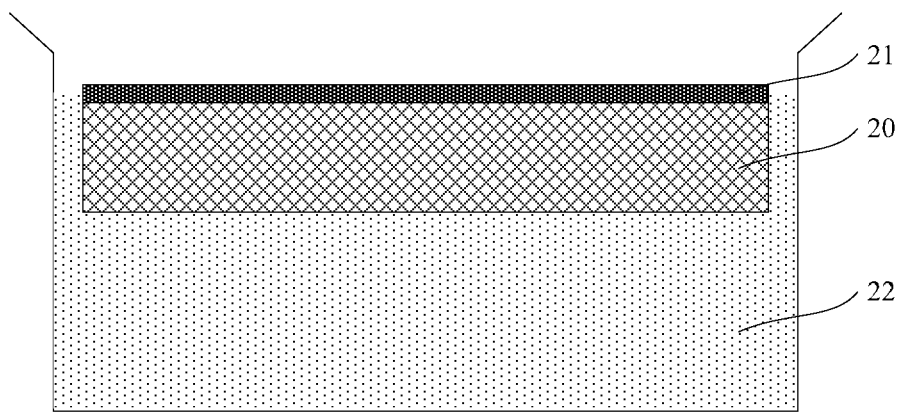
Figure 2C:
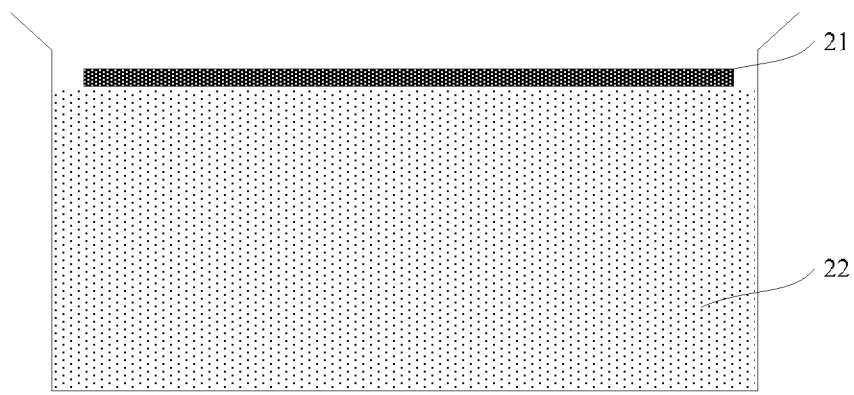
Figure 2D:
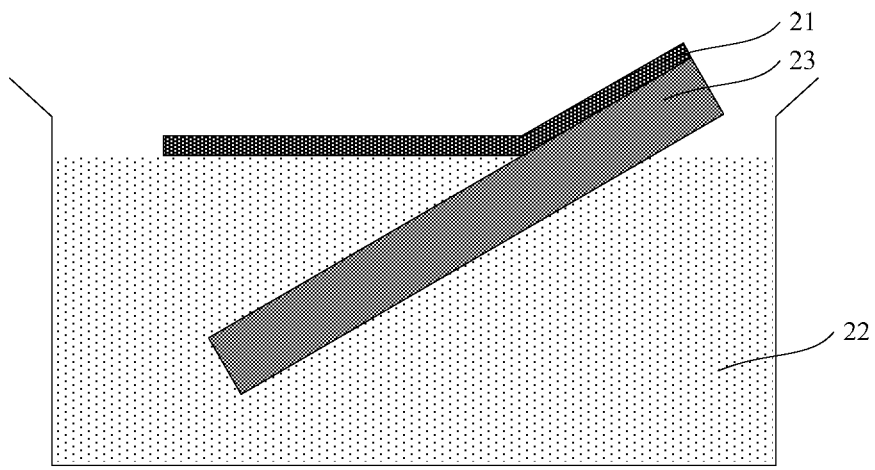
Figure 2E:
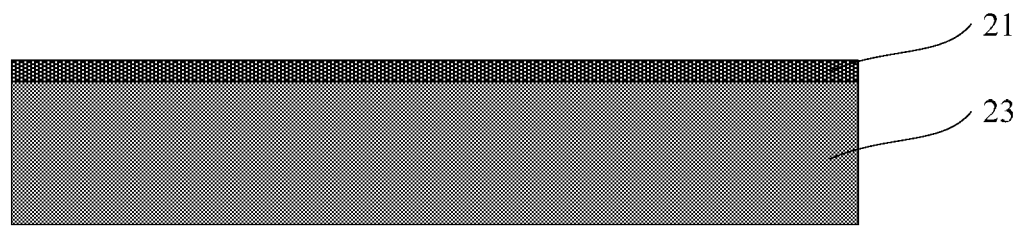

Specifically, firstly, the copper substrate 20 with the intrinsic graphene 21 grown on the surface is put into corrosion solution 22 for 2 h, the corrosion solution 22 is $Fe(NO_3)_3$ solution or $FeCl_3$ solution with certain concentration (such as 0.1 g/ml), as illustrated in FIG. 2b, the intrinsic graphene 21 is separated from the copper substrate 20, as illustrated in FIG. 2c; and secondly, the intrinsic graphene 21 is picked up by the prepared micro heater platform substrate 23, as illustrated in FIG. 2d, so as to obtain the structure illustrated in FIG. 2e.

Figure 2F:
Figure 2G:
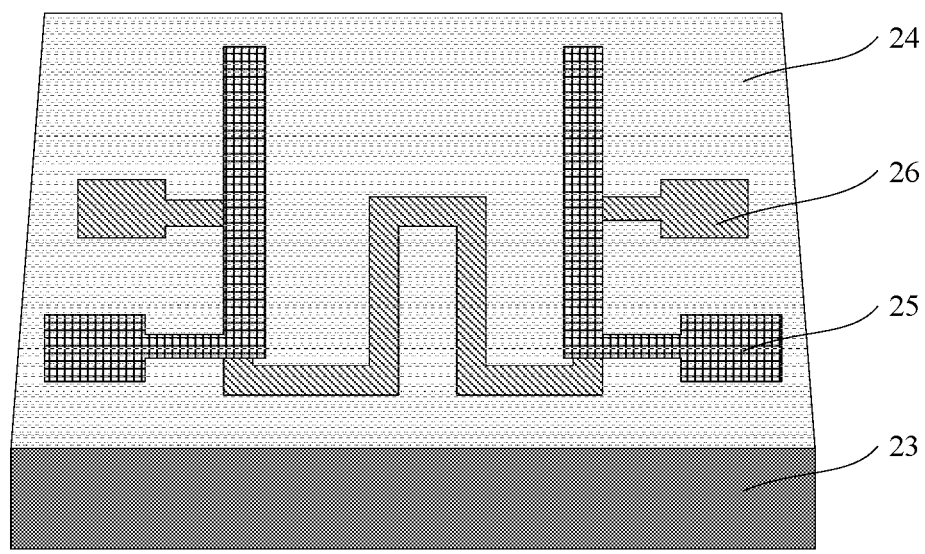

Specifically, after the intrinsic graphene 21 is separated from the copper substrate 20 by the $Fe(NO_3)_3$ solution or $FeCl_3$ solution, and before the intrinsic graphene 21 is picked up by the prepared micro heater platform substrate 23, the method may further comprise the step of putting the intrinsic graphene 21 into HCl solution with certain molar concentration (such as 10%) for corrosion for 1 h, so as to remove residual copper on the surface of the intrinsic graphene 21.

c) The micro heater platform substrate covered with the graphene is put into a chemical vapor deposition reaction furnace.

d) High-purity argon gas with flow rate of 1000 sccm is fed into the reaction furnace for exhausting, and the time is about 10 min.

e) The reaction furnace is heated to 400° C. at temperature increase speed of 5° C./min, and then hydrogen gas with flow rate of 40 sccm is fed and the flow rate of the argon gas is adjusted to 100 sccm.

f) A tubular furnace is heated to 500° C. at the same heating rate, stabilization is performed for 10 min, argon gas with flow rate of 1000 sccm, hydrogen gas with flow rate of 40 sccm and hydrogen sulfide with flow rate of 10 sccm are fed to perform doping to the graphene for 20 min to form sulfur-doped graphene 24.

g) After doping is completed, feeding of hydrogen sulfide is stopped, the reaction furnace is closed for natural cooling, the flow rate of argon gas is kept to be 100 sccm, and the flow rate of hydrogen gas is kept to be 10 sccm in the cooling process.

h) After the temperature of the reaction furnace is decreased to room temperature, gas feeding is stopped and the device is taken out to obtain the nitrogen oxide gas sensor based on sulfur-doped graphene, as illustrated in FIG. 2f. The stereoscopic diagram of the nitrogen oxide gas sensor based on sulfur-doped graphene prepared by this method is illustrated in FIG. 2g, testing of nitrogen dioxide gas may be performed to the sensor after being packaged. From FIG. 2g, it can be seen that the micro heater platform substrate 23 is a single micro heater platform; and the number of the test electrode 25 and the number of the heater 26 both are one, and the test electrode 25 corresponds to the heater 26 from top to bottom.

It needs to be stated that the test electrode 25 and the heater 26 are not visible in FIG. 2g during implementation, and in order to facilitate understanding, the test electrode 25 and the heater 26 in FIG. 2g are shown.

Figure 3A:
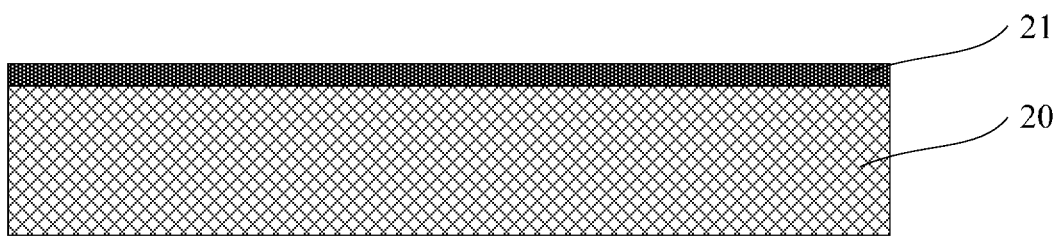
FIG. 3a to FIG. 3h illustrate structural schematic diagrams in each step of a method for preparing a nitrogen oxide gas sensor based on sulfur-doped graphene provided by embodiment 2 of the present disclosure.

Embodiment 2 a) Intrinsic graphene 21 grown on a copper substrate 20 is selected, as illustrated in FIG. 3a.

b) The intrinsic graphene 21 (12 cm*12 cm) is transferred onto a micro heater platform substrate 23 by using a PMMA method. In this embodiment, the micro heater platform substrate 23 is a 6-inch micro heater platform wafer, as illustrated in FIG. 3b to FIG. 3e.

Figure 3B:
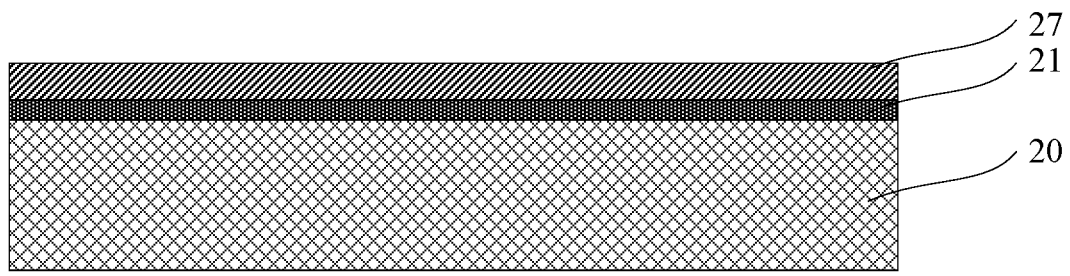
Figure 3C:
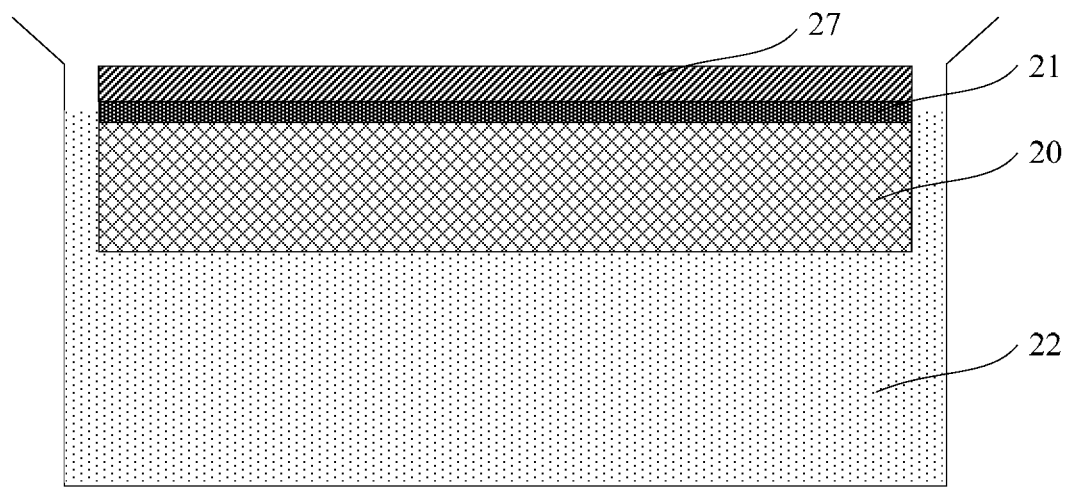
Figure 3D:
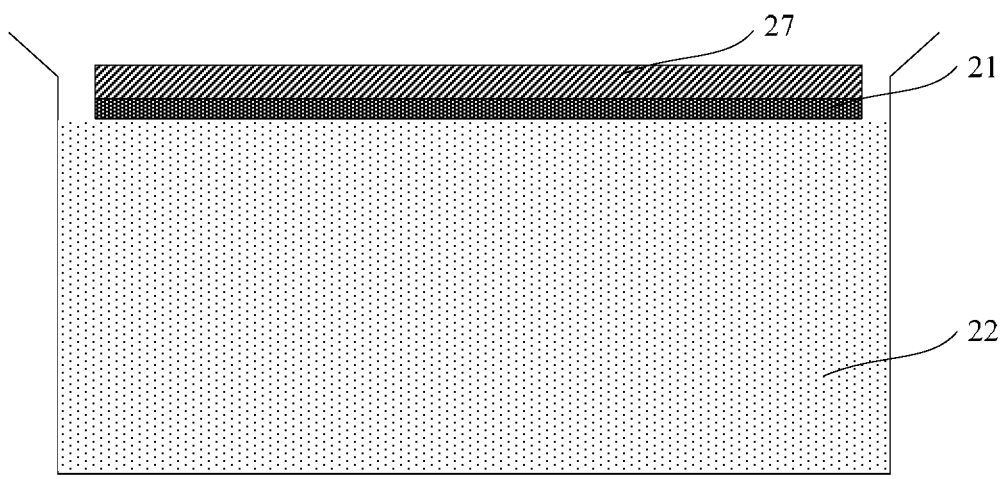
Figure 3E:
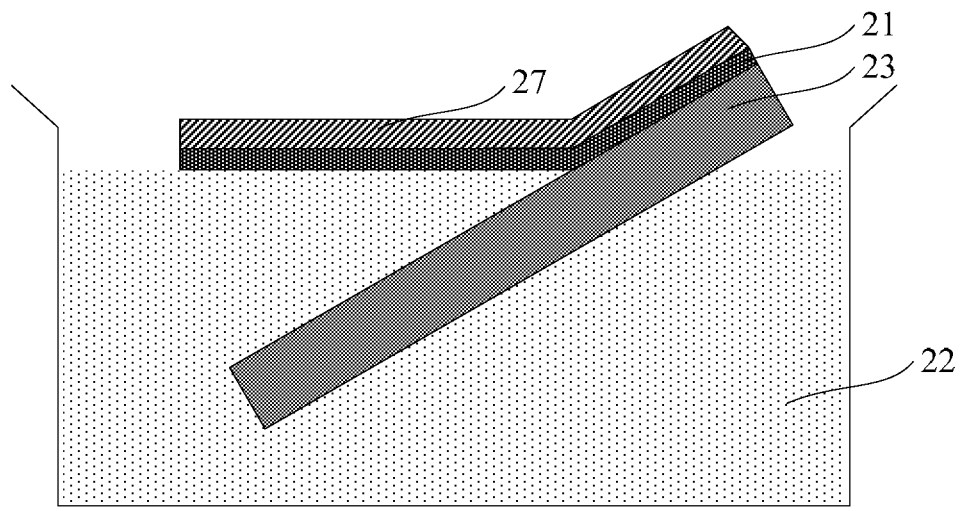
Figure 3F:
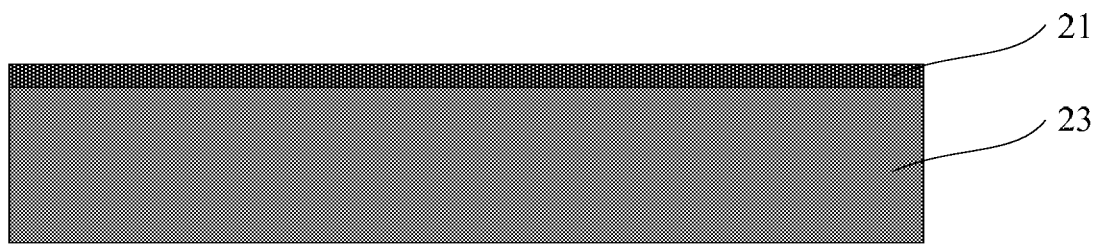

Specifically, firstly, PMMA 27 is uniformly coated onto the surface of the intrinsic graphene 21, and the micro heater platform substrate 23 is heated for 15 min at 150° C., as illustrated in FIG. 3b; secondly, the copper substrate 20 with the intrinsic graphene 21 grown on the surface is put in corrosion solution 22 for 2 h, the corrosion solution 22 is $Fe(NO_3)_3$ solution or $FeCl_3$ solution with certain concentration (such as 0.1 g/ml), as illustrated in FIG. 3c, such that the intrinsic graphene 21 is separated from the copper substrate 20 as illustrated in FIG. 3d; thirdly, the intrinsic graphene 21 is picked up by the prepared micro heater platform substrate 23, as illustrated in FIG. 3e; and finally, PMMA 27 on the surface of the intrinsic graphene 21 is removed by using an annealing method or acetone cleaning method, as illustrated in FIG. 3f.

Figure 3G:
Figure 3H:
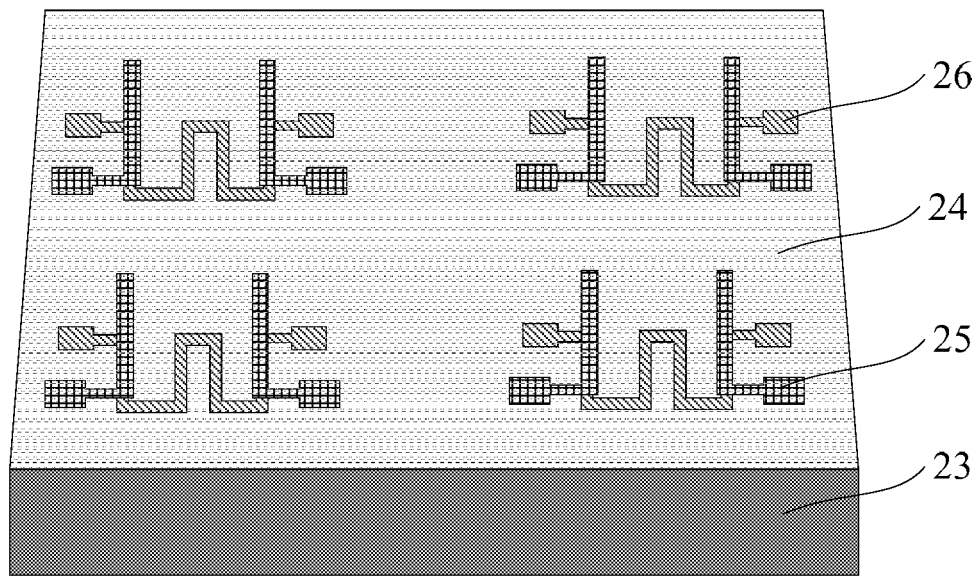

Specifically, after the intrinsic graphene 21 is separated from the copper substrate 20 by $Fe(NO_3)_3$ solution or $FeCl_3$ solution and before the intrinsic graphene 21 is picked up by the prepared micro heater platform substrate 23, the method may further comprise the step of putting the intrinsic graphene 21 into HCl solution with certain molar concentration (such as 10%) for corrosion for 1 h, so as to remove residual copper on the surface of the intrinsic graphene 21.

c) The micro heater platform substrate covered with the graphene is put into a chemical vapor deposition reaction furnace.

d) High-purity argon gas with flow rate of 1000 sccm is fed into the reaction furnace for exhausting, and the time is about 60 min.

e) The reaction furnace is heated to 400° C. at temperature increase speed of 5° C./min, and then hydrogen gas with flow rate of 40 sccm is fed and the flow rate of the argon gas is adjusted to 100 sccm.

f) A tubular furnace is heated to 500° C. at the same temperature increase speed, stabilization is performed for 20 min, argon gas with flow rate of 1000 sccm, hydrogen gas with flow rate of 40 sccm and hydrogen sulfide with flow rate of 10 sccm are fed to perform doping to the graphene for 20 min to form sulfur-doped graphene 24.

g) After doping is completed, feeding of hydrogen sulfide is stopped, the reaction furnace is closed for natural cooling, the flow rate of argon gas is kept to be 100 sccm, and the flow rate of hydrogen gas is kept to be 10 sccm in the cooling process.

h) After the temperature of the reaction furnace is decreased to room temperature, gas feeding is stopped and the wafer is taken out to obtain a wafer level nitrogen oxide gas sensor array based on sulfur-doped graphene, as illustrated in FIG. 3g. The stereoscopic diagram of the wafer level nitrogen oxide gas sensor based on sulfur-doped graphene prepared by adopting this method is as illustrated in FIG. 3h, scribing and packaging are performed to the 6-inch wafer and then testing of nitrogen dioxide gas may be performed. From FIG. 3h, it can be seen that the number of the test electrodes 25 and the number of the heaters 26 both are plural, the plurality of test electrodes 25 and the plurality of heaters 26 are respectively distributed on a first surface and a second surface of the micro heater platform substrate 23 in an array, and the test electrodes 25 correspond to the heaters 26 one to one from top to bottom.

It needs to be stated that the test electrodes 25 and the heaters 26 are not visible in FIG. 3h during implementation, and in order to facilitate understanding, the test electrode 25 and the heater 26 in FIG. 3h are shown.

Embodiment 3

Figure 4:
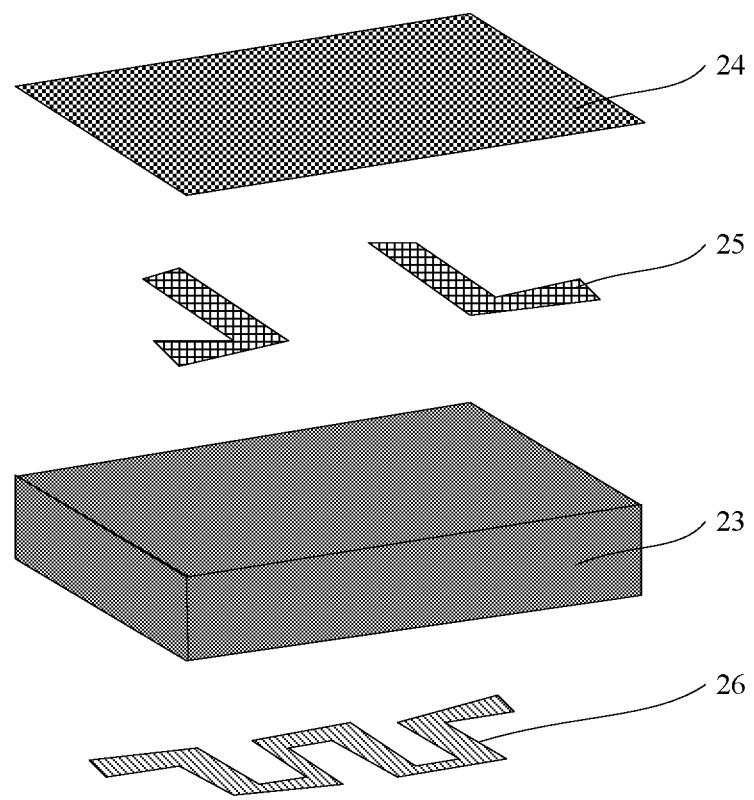
FIG. 4 illustrates an exploded structural schematic diagram of a nitrogen oxide gas sensor based on sulfur-doped graphene provided by embodiment 3 of the present disclosure.

Please referring to FIG. 4, the present disclosure further provides a nitrogen oxide gas sensor based on sulfur-doped graphene, the nitrogen oxide gas sensor based on sulfur-doped graphene is prepared by adopting the preparation method in the above-mentioned solution, and the nitrogen oxide gas sensor based on sulfur-doped graphene comprises: a micro heater platform substrate 23 and sulfur-doped graphene 24;

a test electrode 25 and a heater 26 are provided on the micro heater platform substrate 23; and the sulfur-doped graphene 24 at least covers the test electrode 25.

As an example, the test electrode 25 and the heater 26 are not in direct contact, and the test electrode 25 and the heater 26 may be located on different surfaces of the micro heater platform substrate 23 or located on the same surface of the micro heater platform substrate 23; and when the test electrode 25 and the heater 26 are located on the same surface of the micro heater platform substrate 23, the test electrode 25 and the heater 26 are isolated through an insulating layer.

In one example, the micro heater platform substrate 23 comprises a first surface and a second surface; the test electrode 25 is located on the first surface and the heater 26 is located on the second surface; and the sulfur-doped graphene 24 is located on the first surface of the micro heater platform substrate 23 and covers the test electrode 25 and the first surface of the micro heater platform substrate 23.

As an example, the micro heater platform substrate 23 may be a single micro heater platform or a wafer level substrate; and when the micro heater platform substrate 23 is a wafer level substrate, the wafer level substrate may be but not limited to 4-inch, 8-inch, 12-inch and 16-inch wafers batch-manufactured industrially. FIG. 4 takes the micro heater platform substrate 23 which is a single micro heater platform substrate as an example, the corresponding stereoscopic structural schematic diagram therefor is as illustrated in FIG. 2g, and for details, refer to FIG. 2g and the related content, which are not repetitively described here. The stereoscopic structural schematic diagram when the micro heater platform substrate 23 is a wafer level substrate is illustrated in FIG. 3h, and for details, please refer to FIG. 3h and the related content, which are not repetitively described here.

As an example, the test electrode 25 may be but not limited to an interdigital electrode.

To sun up, the present disclosure provides a nitrogen oxide gas sensor based on sulfur-doped graphene and a method for preparing the same, wherein the method comprises the following steps: 1) providing graphene and a micro heater platform substrate, and transferring the graphene onto the micro heater platform substrate; 2) putting the micro heater platform substrate covered with the graphene into a chemical vapor deposition reaction furnace; 3) performing gas feeding and exhausting treatment to the reaction furnace by using inert gas; 4) simultaneously feeding insert gas and hydrogen gas into the reaction furnace at first temperature; 5) feeding inert gas, hydrogen gas and sulfur source gas into the reaction furnace at second temperature for reaction to perform sulfur doping to the graphene; and 6) stopping feeding the sulfur source gas, and performing cooling to the reaction furnace in a hydrogen gas and insert gas shielding atmosphere. The method provided by the present disclosure may adopt a wafer level substrate, which can realize wafer level preparation, achieve the level of batch manufacturing and greatly reduce the production cost; and the nitrogen oxide gas sensor based on sulfur-doped graphene provided by the present disclosure has relatively high sensitivity and selectivity to nitrogen oxide gas molecules, can effectively reduce influences of other gases such as vapor on detection, and can improve the detection accuracy.

The above-mentioned embodiments are just used for exemplarily describing the principle and effect of the present disclosure instead of limiting the present disclosure. One skilled in the art may make modifications or changes to the above-mentioned embodiments without departing from the spirit and scope of the present disclosure. Therefore, all equivalent modifications or changes made by those who have common knowledge in the art without departing from the spirit and technical thought disclosed by the present disclosure shall be still covered by the claims of the present disclosure.

What is claimed is:

1. A method for preparing nitrogen oxide gas sensor based on sulfur-doped graphene, comprising:
   1) providing an intrinsic graphene grown on a copper substrate and a micro heater platform substrate, and transferring the intrinsic graphene from the intrinsic graphene grown on a copper substrate onto the micro heater platform substrate;
   2) putting the micro heater platform substrate covered with the intrinsic graphene into a chemical vapor deposition reaction furnace;
   3) performing gas feeding and exhausting treatment to the reaction furnace by using inert gas;
   4) simultaneously feeding inert gas and hydrogen gas into the reaction furnace at a first temperature;
   5) feeding inert gas, hydrogen gas and sulfur source gas into the reaction furnace at a second temperature for reaction to perform sulfur doping to the graphene; and
   6) stopping feeding the sulfur source gas, and performing cooling to the reaction furnace in a hydrogen gas and insert gas shielding atmosphere.

2. The method for preparing nitrogen oxide gas sensor based on sulfur-doped graphene according to claim 1, wherein, in step 1), the intrinsic graphene grown on a copper substrate is placed into corrosion solution for 2 hours, wherein the corrosion solution is $Fe(NO_3)_3$ solution or $FeCl_3$ solution with a concentration of 0.1 g/ml, so that the intrinsic graphene is separated from the copper substrate, and then the intrinsic graphene is picked up by the micro heater platform substrate.

3. The method for preparing nitrogen oxide gas sensor based on sulfur-doped graphene according to claim 1, wherein, in step 1), the micro heater platform substrate is a single micro heater platform or a wafer level substrate.

4. The method for preparing nitrogen oxide gas sensor based on sulfur-doped graphene according to claim 1, wherein, in step 1), a test electrode and a heater are provided on the micro heater platform substrate, and the intrinsic graphene at least covers the test electrode.

5. The method for preparing nitrogen oxide gas sensor based on sulfur-doped graphene according to claim 1, wherein, in step 1), the intrinsic graphene is transferred onto the micro heater platform substrate by adopting a direct transfer method or PMMA method.

6. The method for preparing nitrogen oxide gas sensor based on sulfur-doped graphene according to claim 1, wherein, in step 3), the flow rate of the inert gas is 500 sccm-5000 sccm, and the gas feeding and exhausting treatment time is 2 min-30 min.

7. The method for preparing nitrogen oxide gas sensor based on sulfur-doped graphene according to claim 1, wherein, in step 4), the first temperature is 200° C.-700° C.; the flow rate of mixed gas of the hydrogen gas and the inert gas is 100 sccm-5000 sccm; and the mixing ratio of the hydrogen gas to the inert gas is 10%-90%.

8. The method for preparing nitrogen oxide gas sensor based on sulfur-doped graphene according to claim 1, wherein, in step 5), the second temperature is 300° C.-900° C.; the flow rate of the inert gas is 500 sccm-5000 sccm, the flow rate of the hydrogen gas is 10 sccm-100 sccm and the flow rate of the sulfur source gas is 0.5 sccm-50 sccm; and the doping time is 10 min-50 min.

9. The method for preparing nitrogen oxide gas sensor based on sulfur-doped graphene according to claim 1, wherein the sulfur source gas comprises one or more of hydrogen sulfide and carbonyl sulfide.

10. The method for preparing nitrogen oxide gas sensor based on sulfur-doped graphene according to claim 1, wherein, in step 5), temperature is increased from the first temperature to the second temperature, the temperature is kept at the second temperature for 5 min-20 min, and then the sulfur source gas is fed into the reaction furnace.

11. The method for preparing nitrogen oxide gas sensor based on sulfur-doped graphene according to claim 1, wherein, in step 6), the flow rate of the inert gas is 50 sccm-300 sccm, and the flow rate of the hydrogen gas is 10sccm-40 sccm.

* * * * *